United States Patent
Ibrahim et al.

(10) Patent No.: US 9,704,701 B2
(45) Date of Patent: Jul. 11, 2017

(54) METHOD AND DEVICE FOR ION MOBILITY SEPARATIONS

(71) Applicants: Yehia M. Ibrahim, Richland, WA (US); Sandilya V. B. Garimella, Richland, WA (US); Richard D. Smith, Richland, WA (US)

(72) Inventors: Yehia M. Ibrahim, Richland, WA (US); Sandilya V. B. Garimella, Richland, WA (US); Richard D. Smith, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 14/851,935

(22) Filed: Sep. 11, 2015

(65) Prior Publication Data

US 2017/0076931 A1    Mar. 16, 2017

(51) Int. Cl.
H01J 49/26 (2006.01)
H01J 49/40 (2006.01)
G01N 27/62 (2006.01)

(52) U.S. Cl.
CPC ............ *H01J 49/26* (2013.01); *G01N 27/622* (2013.01); *H01J 49/40* (2013.01)

(58) Field of Classification Search
None
See application file for complete search history.

(56) References Cited

U.S. PATENT DOCUMENTS

| | | | |
|---|---|---|---|
| 4,777,363 A | 10/1988 | Eiceman et al. | |
| 5,572,035 A | 11/1996 | Franzen | |
| 5,834,771 A | 11/1998 | Yoon et al. | |
| 6,107,328 A | 8/2000 | Parsons | |
| 6,417,511 B1 | 7/2002 | Russ, IV et al. | |
| 6,960,760 B2 | 11/2005 | Bateman et al. | |
| 7,365,317 B2 * | 4/2008 | Whitehouse | H01J 49/42 250/287 |
| 7,391,021 B2 | 6/2008 | Stoermer et al. | |
| 7,786,435 B2 | 8/2010 | Whitehouse et al. | |

(Continued)

FOREIGN PATENT DOCUMENTS

EP    1566828 A2    2/2005
EP    1825495 B1    11/2011
(Continued)

OTHER PUBLICATIONS

International Search Report/Written Opinion for International Application No. PCT/US2016/030455, International Filing Date May 2, 2016, Date of Mailing Jul. 25, 2016.
(Continued)

*Primary Examiner* — Jack Berman
(74) *Attorney, Agent, or Firm* — Mintz Levin Cohn Ferris Glovsky and Popeo, P.C.; William C. Geary; Michael A. Mattoni

(57) ABSTRACT

Methods and devices for ion separations or manipulations in gas phase are disclosed. The device includes a single non-planar surface. Arrays of electrodes are coupled to the surface. A combination of RF and DC voltages are applied to the arrays of electrodes to create confining and driving fields that move ions through the device. The DC voltages are static DC voltages or time-dependent DC potentials or waveforms.

53 Claims, 10 Drawing Sheets

(56) References Cited

U.S. PATENT DOCUMENTS

| | | | |
|---|---|---|---|
| 7,838,826 | B1 | 11/2010 | Park |
| 7,888,635 | B2 | 2/2011 | Belov et al. |
| 7,928,375 | B1 | 4/2011 | Mangan et al. |
| 8,049,169 | B2 | 11/2011 | Satake et al. |
| 8,222,597 | B2 | 7/2012 | Kim et al. |
| 8,835,839 | B1 | 9/2014 | Anderson et al. |
| 2003/0132379 | A1 | 7/2003 | Li |
| 2004/0026611 | A1 | 2/2004 | Bateman et al. |
| 2004/0089803 | A1 | 5/2004 | Foley |
| 2007/0138384 | A1 | 6/2007 | Keiser |
| 2011/0049357 | A1 | 3/2011 | Giles |
| 2011/0192969 | A1 | 8/2011 | Verentchikov |
| 2015/0028200 | A1 | 1/2015 | Green et al. |

FOREIGN PATENT DOCUMENTS

| | | |
|---|---|---|
| EP | 2913839 A1 | 2/2014 |
| JP | 2002015699 A | 1/2002 |
| WO | 2015056872 A1 | 4/2015 |

OTHER PUBLICATIONS

International Search Report/Written Opinion for International Application No. PCT/US14/11291, International Filing Date Jan. 13, 2014, Date of Mailing Jun. 6, 2014.

PCT Recordation of Search History for International Application No. PCT/US14/11291, International Filing Date Jan. 13, 2014, Date during which the search was conducted May 15, 2014, Date of Completion of Recordation of Search History Form May 22, 2014.

Ibrahim, Y. M., et al., Development of a new ion mobility (quadrupole) time-of-flight mass spectrometer, International Journal of Mass Spectrometry, 2014, 377, 655-662.

Smith, D. P., et al., Deciphering drift time measurements of ion mobilities using a travelling wave ion guide, International Journal of Mass Spectrometry, 15, 2009, 113-130.

Giles, K., et al., A method for direct measurement of ion mobilities using a travelling wave ion guide, International Journal of Mass Spectrometry, 298, 2010, 10-16.

Pringle, S. D., et al., An investigation of the mobility separation of some peptide and protein ions using a new hybrid quadrupole/travelling wave IMS/os-ToF instrument, International Journal of Mass Spectrometry, 261, 2007, 1-12.

Webb, I. K., et al., Mobility-Resolved Ion Selection in Uniform Drift Field Ion Mobility Spectrometry/Mass Spectrometry: Dynamic Switching in Structures for Lossless Ion Manipulations, Analytical Chemistry, 86, 2014, 9632-9637.

Shvartsburg, A. A., et al., Fundamentals of Traveling Wave Ion Mobility Spectrometry, Analytical Chemistry, 80, 2008, 9689-9699.

Giles, K., et al., Applications of a travelling wave-based radio-frequency-only stacked ring ion guide, Rapid Communications in Mass Spectrometry, 18, 2004, 2401-2414.

Zhong, Y., et al., Characterizing the resolution and accuracy of a second-generation traveling-wave ion mobility separator for biomolecular ions, Analyst, 136, 2011, 3534-3541.

Merenbloom, S. I., et al., Effects of Select Anions from the Hofmeister Series on the Gas-Phase Conformations of Protein Ions Measured with Traveling-Wave Ion Mobility Spectrometry/Mass Spectrometry, Journal of the American Society for Mass Spectrometry, 22, 2011, 1978-1990.

Giles, K., et al., Enhancements in travelling wave ion mobility resolution, Rapid Communications in Mass Spectrometry, 25, 2011, 1559-1566.

Garimella, S. B. V., et al., Simulation of Electric Potentials and Ion Motion in Planar Electrode Structures for Lossless Ion Manipulations (SLIM), Journal of the American Society for Mass Spectrometry, 25, 2014, 1890-1896.

Tolmachev, A. V., et al., Characterization of Ion Dynamics in Structures for Lossless Ion Manipulations, Analytical Chemistry, 86, 2014, 9162-9168.

Webb, I. K., et al., Experimental Evaluation and Optimization of Structures for Lossless Ion Manipulations for Ion Mobility Spectrometry with Time-of-Flight Mass Spectrometry, Analytical Chemistry, 86, 2014, 9169-9176.

Zhang, X., et al., Ion Trapping, Storage, and Ejection in Structures for Lossless Ion Manipulations, Analytical Chemistry, 87, 2015, 6010-6016.

Glaskin, R. S., et al., Ion Trapping for Ion Mobility Spectrometry Measurements in a Cyclical Drift Tube, Analytical Chemistry, 85, 2013, 7003-7008.

Sobott, F., et al., Tandem Mass Spectrometer for Improved Transmission and Analysis of Large Macromolecular Assemblies, Analytical Chemistry, 74, 2002, 1402-1407.

\* cited by examiner

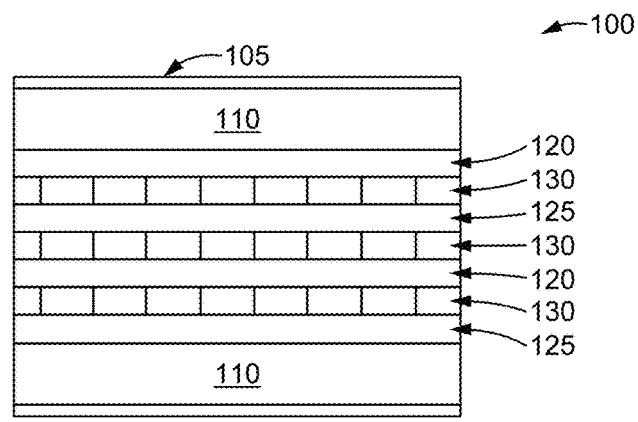
Fig. 1A
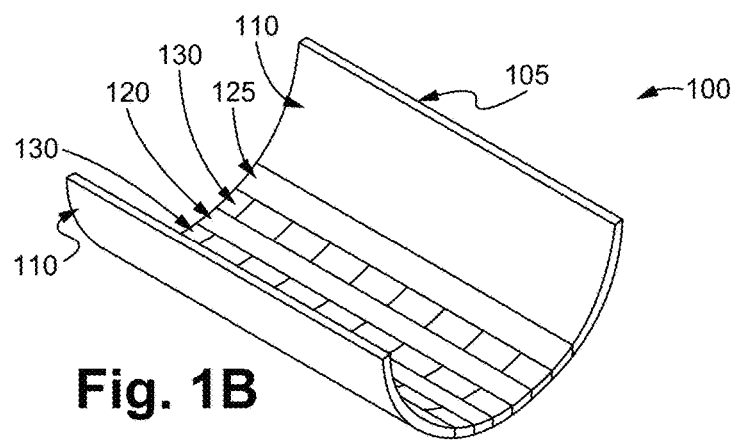
Fig. 1B
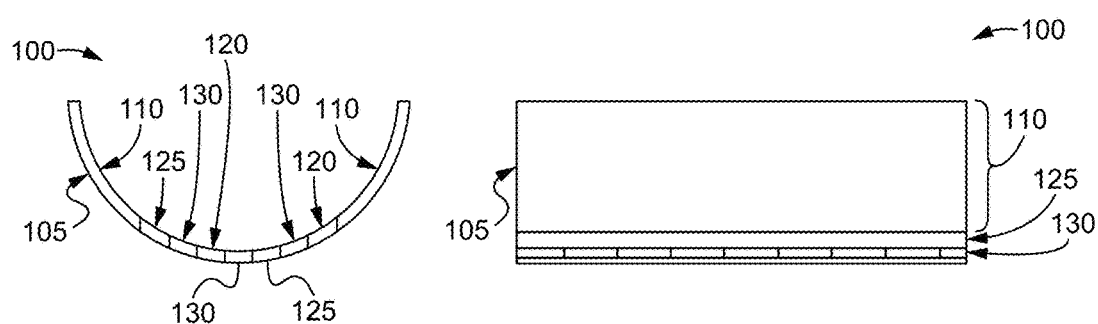
Fig. 1C
Fig. 1D

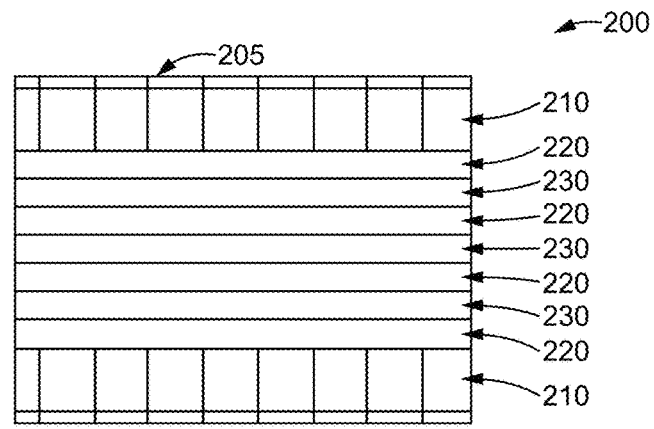
Fig. 2A
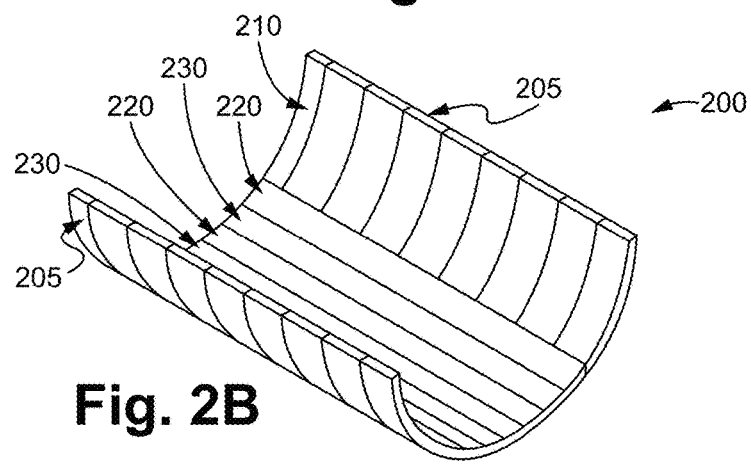
Fig. 2B
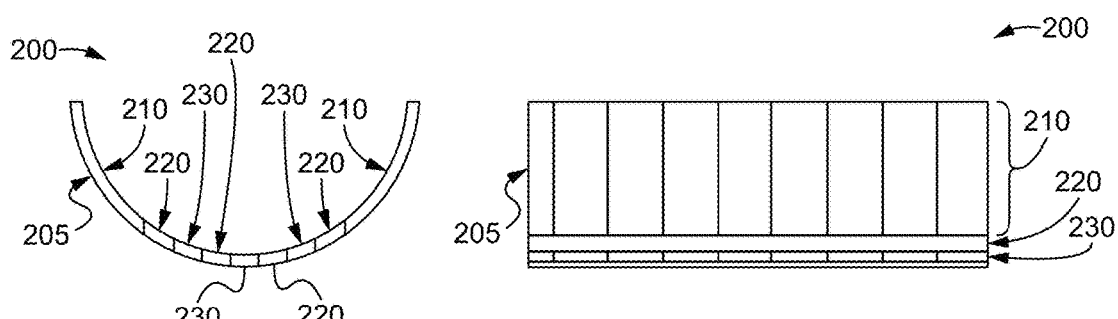
Fig. 2C
Fig. 2D

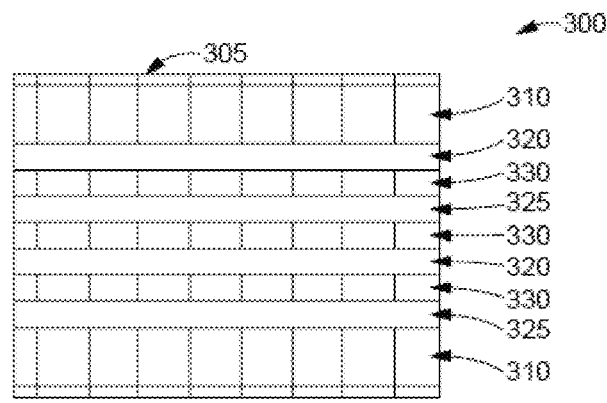
Fig. 3A
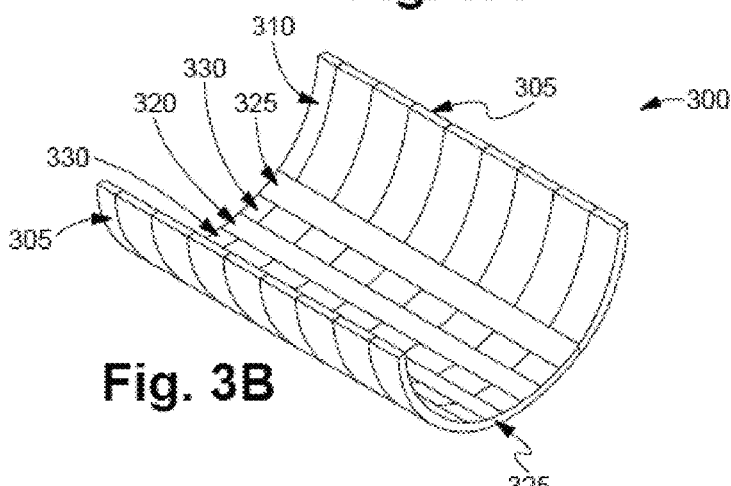
Fig. 3B
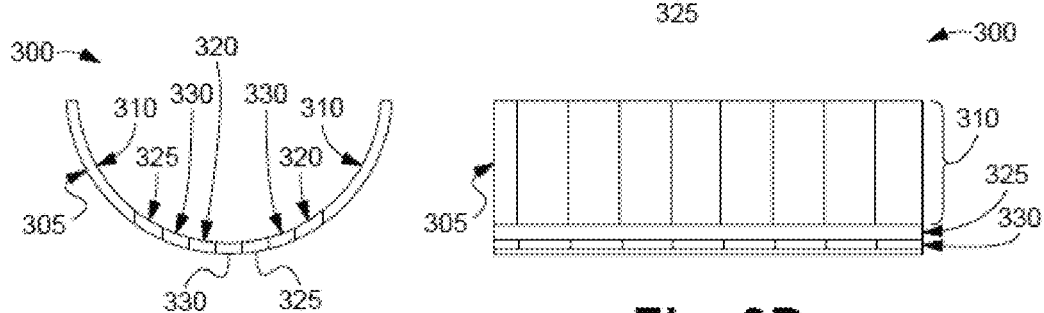
Fig. 3C
Fig. 3D

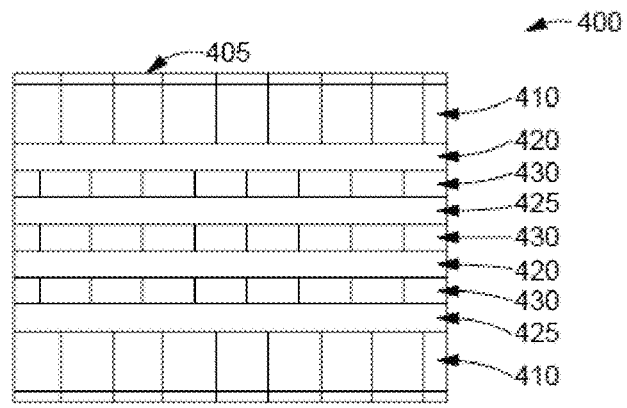
Fig. 4A
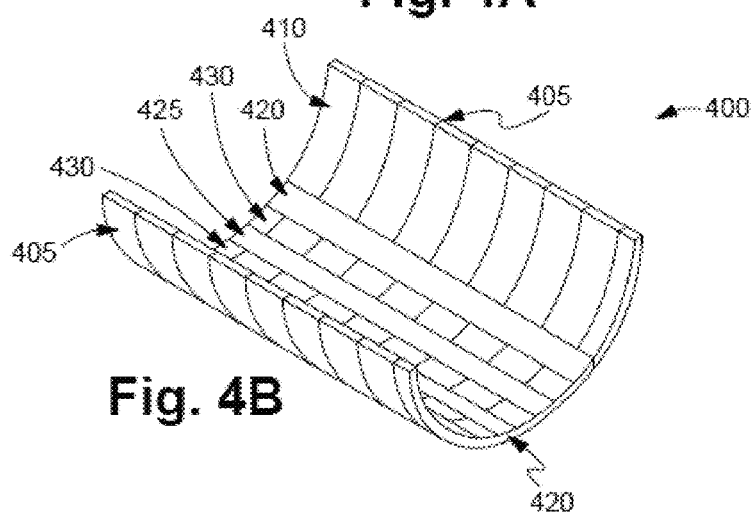
Fig. 4B
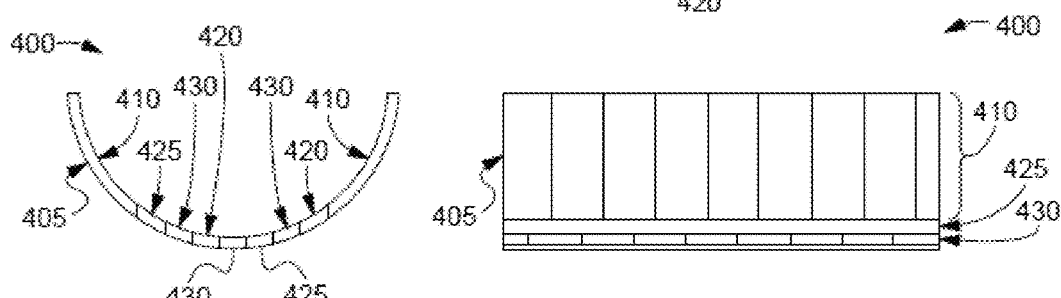
Fig. 4C  Fig. 4D

METHOD AND DEVICE FOR ION MOBILITY SEPARATIONS

STATEMENT REGARDING FEDERALLY SPONSORED RESEARCH OR DEVELOPMENT

This invention was made with Government support under Contract DE-AC0576RLO1830 awarded by the U.S. Department of Energy. The Government has certain rights in the invention.

TECHNICAL FIELD

This invention relates to ion mobility separations and other ion manipulations in the gas phase. More specifically, this invention relates to an ion mobility separation method and ion manipulations in a device having a single, non-planar surface containing electrodes.

BACKGROUND

The utility of mass spectrometry expands with the capability to conduct more complex ion manipulations. Current ion mobility technologies and ion manipulations rely on surrounding surfaces that serve to define the electric fields. However, these approaches can become ineffective when, for example, trying to miniaturize these devices for field deployment. In addition, it is extremely difficult to achieve high ion mobility spectrometry (IMS) resolution by extending the drift length traveled by ions in a reasonable and practical physical length. Hence, the utility of IMS is hindered by conventional ion optics designs.

What is needed is an ion mobility separation or manipulation device with an open structure, including an ion separation channel, and which also prevents ion losses.

SUMMARY

The present invention is directed to an ion mobility separation or manipulation device that includes a single surface. The single surface is non-planar or not flat. The device also includes arrays of electrodes coupled to the surface. The device further includes a combination of RF and DC voltages applied to arrays of electrodes to create confining and driving fields that move ions through the device. The surface can have, in one embodiment, arrays of electrodes on each side of the surface.

In one embodiment, one or more electrodes or others surfaces external to the device can help partially or fully define or affect the electric fields created by the electrodes on the surface. These external electrodes or surfaces, which have voltages applied to them, allow different or more complex fields to be established or created. This would allow, for example, one array of electrodes on the surface to be turned off while the other array is turned on. This can be useful for, among other things, peak compression or the bunching of ions. In one embodiment, the arrays of electrodes coupled to the surface extend above the surface, and may also vary in the distance above the surface. Further, the one or more arrays of electrodes coupled to the surface can be turned on or turned off by the external surfaces and/or electrodes.

The single, non-planar surface can be of many different shapes. The surface can have a curved, cylindrical, spiral, funnel, hemispherical, elliptical, or non-symmetrical shape.

In one embodiment, a transparent enclosure or cover is disposed on the device. A voltage can be applied to the cover to guard against interfering potential from, e.g., ground or nearby electronics. In one embodiment, the device is located in a partially or completely transparent enclosure or cover.

In one embodiment, the arrays of electrodes include one or more arrays of inner RF electrodes and a plurality of arrays of outer DC electrodes. The inner array of RF electrodes and the outer arrays of DC electrodes extend substantially along the length of the surface. In one embodiment, a first outer array of DC electrodes is positioned on one side of the inner array of RF electrodes, and a second outer array of DC electrodes is positioned on the other side of the inner array of electrodes.

In one embodiment, the DC voltages are applied to the first and second outer electrodes arrays, and the RF voltages are applied to the inner array of electrodes.

In one embodiment, the RF waveform on at least one inner electrode array is out of phase with RF waveform on a neighboring inner RF electrode array. The RF voltage applied to each inner RF electrode array may be phase shifted with its neighboring inner electrode array to form a pseudopotential. In one embodiment, the RF voltage applied to the inner electrode array is approximately 180 degrees out of phase with its neighboring inner electrode array to form the pseudopotential.

The device may further comprise one or more arrays of inner DC electrodes that extend substantially along the length of the surface, in either a linear or non-linear path. Each inner array of DC electrodes is positioned between an adjacent pair of the RF electrode arrays. A RF waveform on at least one inner array of RF electrodes is out of phase with RF waveform on a neighboring or adjacent inner array of RF electrodes.

In one embodiment, a first DC voltage applied to the outer array of DC electrodes is the same, and a second DC voltage applied to the inner array of DC electrodes is a DC gradient or different across the inner DC arrays.

In one embodiment, a first DC voltage applied to the outer array of DC electrodes is different across the outer array or is a DC gradient, and a second DC voltage applied to the inner array of DC electrodes is a DC gradient or different across the inner DC arrays.

The first DC voltage may have a higher or lower amplitude than the second DC field.

In one embodiment, the inner array of DC electrodes is misaligned or offset from the outer array of electrodes.

In one embodiment, a DC voltage is superimposed on at least one of the inner arrays of RF electrodes.

The device may be coupled to at least one of the following: a charge detector, ion image detector, an optical detector, and a mass spectrometer.

In one embodiment, the ions are introduced from outside the device at an angle to the device.

The ions may be formed inside or outside of the device using at least one of the following: photoionization, Corona discharge, laser ionization, electron impact, field ionization, chemical ionization, and electrospray.

The DC voltages may be static DC voltages or time-dependent DC potentials or waveforms.

In one embodiment, the surface is formed by curving a flexible printed circuit board material, three-dimensional printing, or other means to deposit conductive material on a non-conductive surface.

In another embodiment of the present invention, a method of moving and separating ions in gas phase is disclosed. The method includes coupling arrays of electrodes to a single, non-planar surface. The method also includes applying a combination of RF and DC voltages to the arrays of electrodes to create confining and driving fields that move ions through the single curved or non-planar surface.

In another embodiment of the present invention, an ion mobility separation device is disclosed. The device includes a single, non-planar surface. The device also includes arrays of electrodes which include one or more arrays of inner RF electrodes and a plurality of arrays of outer DC electrodes. The inner array of RF electrodes and the outer array of DC electrodes extend substantially along the length of the surface. A first and second outer array of DC electrodes is positioned on either side of the inner array of RF electrodes. The device further includes one or more arrays of inner DC electrodes that extend substantially along the length of the surface. Each inner array of DC electrodes is positioned between an adjacent pair of inner RF electrode arrays. A combination of RF and DC voltages are applied to the arrays of electrodes to create confining and driving fields that move ions through the device.

In one embodiment, a RF waveform on at least one inner array of RF electrodes is out of phase with RF waveform on a neighboring or adjacent inner array of RF electrodes.

A first DC voltage applied to the outer array of DC electrodes is the same or different, and a second DC voltage applied to the inner array of DC electrodes is a DC gradient or different across the inner DC arrays.

In another embodiment of the present invention, an ion mobility device is disclosed. The device includes a single, non-planar surface. The device also includes arrays of inner RF electrodes and a plurality of arrays of outer DC electrodes, coupled to the single surface, wherein the inner array of RF electrodes and the outer array of DC electrodes extend substantially along the length of the single surface. A first and second outer array of DC electrodes is positioned on either side of the inner array of RF electrodes. A combination of RF and DC voltages applied to the arrays of electrodes to create confining and driving fields that move ions through the device, and a DC field is superimposed on the inner arrays of RF electrodes to further confine and move the ions through the device.

In another embodiment, the device can include two or more non-planar surfaces with different orientations to each other that provide a "waterfall" effect of the ions moving through each surface.

BRIEF DESCRIPTION OF THE DRAWINGS

FIG. 1A is a top view schematic diagram of an ion mobility device having a single curved or non-planar surface containing arrays of outer and inner DC electrodes and arrays of RF electrodes of opposite phase on either side of the inner DC electrodes, in accordance with one embodiment of the present invention.

FIG. 1B is a perspective view schematic diagram of an ion mobility device having a single curved or non-planar surface containing arrays of outer and inner DC electrodes and arrays of RF electrodes of opposite phase on either side of the inner DC electrodes, in accordance with one embodiment of the present invention.

FIG. 1C is a front view schematic diagram of an ion mobility device having a single curved or non-planar surface containing arrays of outer and inner DC electrodes and arrays of RF electrodes of opposite phase on either side of the inner DC electrodes, in accordance with one embodiment of the present invention.

FIG. 1D is a side view schematic diagram of an ion mobility device having a single curved or non-planar surface containing arrays of outer and inner DC electrodes and arrays of RF electrodes of opposite phase on either side of the inner DC electrodes, in accordance with one embodiment of the present invention.

FIG. 2A is a top view schematic diagram of an ion mobility device having a single curved or non-planar surface containing arrays of outer DC electrodes and inner RF electrodes with a superimposed DC field on the inner array of RF electrodes, in accordance with one embodiment of the present invention.

FIG. 2B is a perspective view schematic diagram of an ion mobility device having a single curved or non-planar surface containing arrays of outer DC electrodes and inner RF electrodes with a superimposed DC field on the inner array of RF electrodes, in accordance with one embodiment of the present invention.

FIG. 2C is a front view schematic diagram of an ion mobility device having a single curved or non-planar surface containing arrays of outer DC electrodes and inner RF electrodes with a superimposed DC field on the inner array of RF electrodes, in accordance with one embodiment of the present invention.

FIG. 2D is a side view schematic diagram of an ion mobility device having a single curved or non-planar surface containing arrays of outer DC electrodes and inner RF electrodes with a superimposed DC field on the inner array of RF electrodes, in accordance with one embodiment of the present invention.

FIG. 3A is a top view schematic diagram of an ion mobility device having a single curved or non-planar surface containing arrays of outer and inner DC electrodes with different DC fields or a DC gradient applied across the electrodes and arrays of RF electrodes of opposite phase on either side of the inner DC electrodes, in accordance with one embodiment of the present invention.

FIG. 3B is a perspective view schematic diagram of an ion mobility device having a single curved or non-planar surface containing arrays of outer and inner DC electrodes with different DC fields or a DC gradient applied across the electrodes and arrays of RF electrodes of opposite phase on either side of the inner DC electrodes, in accordance with one embodiment of the present invention.

FIG. 3C is a front view schematic diagram of an ion mobility device having a single curved or non-planar surface containing arrays of outer and inner DC electrodes with different DC fields or a DC gradient applied across the electrodes and arrays of RF electrodes of opposite phase on either side of the inner DC electrodes, in accordance with one embodiment of the present invention.

FIG. 3D is a side view schematic diagram of an ion mobility device having a single curved or non-planar surface containing arrays of outer and inner DC electrodes with different DC fields or a DC gradient applied across the electrodes and arrays of RF electrodes of opposite phase on either side of the inner DC electrodes, in accordance with one embodiment of the present invention.

FIG. 4A is a top view schematic diagram of an ion mobility device having a single curved or non-planar surface containing arrays of misaligned or offset outer and inner DC electrodes with different DC fields or a DC gradient applied across the electrodes and arrays of RF electrodes of opposite phase on either side of the inner DC electrodes, in accordance with one embodiment of the present invention.

FIG. 4B is a perspective view schematic diagram of an ion mobility device having a single curved or non-planar surface containing arrays of misaligned or offset outer and inner DC electrodes with different DC fields or a DC gradient applied across the electrodes and arrays of RF electrodes of opposite phase on either side of the inner DC electrodes, in accordance with one embodiment of the present invention.

FIG. 4C is a front view schematic diagram of an ion mobility device having a single curved or non-planar surface containing arrays of misaligned or offset outer and inner DC electrodes with different DC fields or a DC gradient applied across the electrodes and arrays of RF electrodes of opposite phase on either side of the inner DC electrodes, in accordance with one embodiment of the present invention.

FIG. 4D is a side view schematic diagram of an ion mobility device having a single curved or non-planar surface containing arrays of misaligned or offset outer and inner DC electrodes with different DC fields or a DC gradient applied across the electrodes and arrays of RF electrodes of opposite phase on either side of the inner DC electrodes, in accordance with one embodiment of the present invention.

DETAILED DESCRIPTION OF THE PREFERRED EMBODIMENTS

Figure 5:
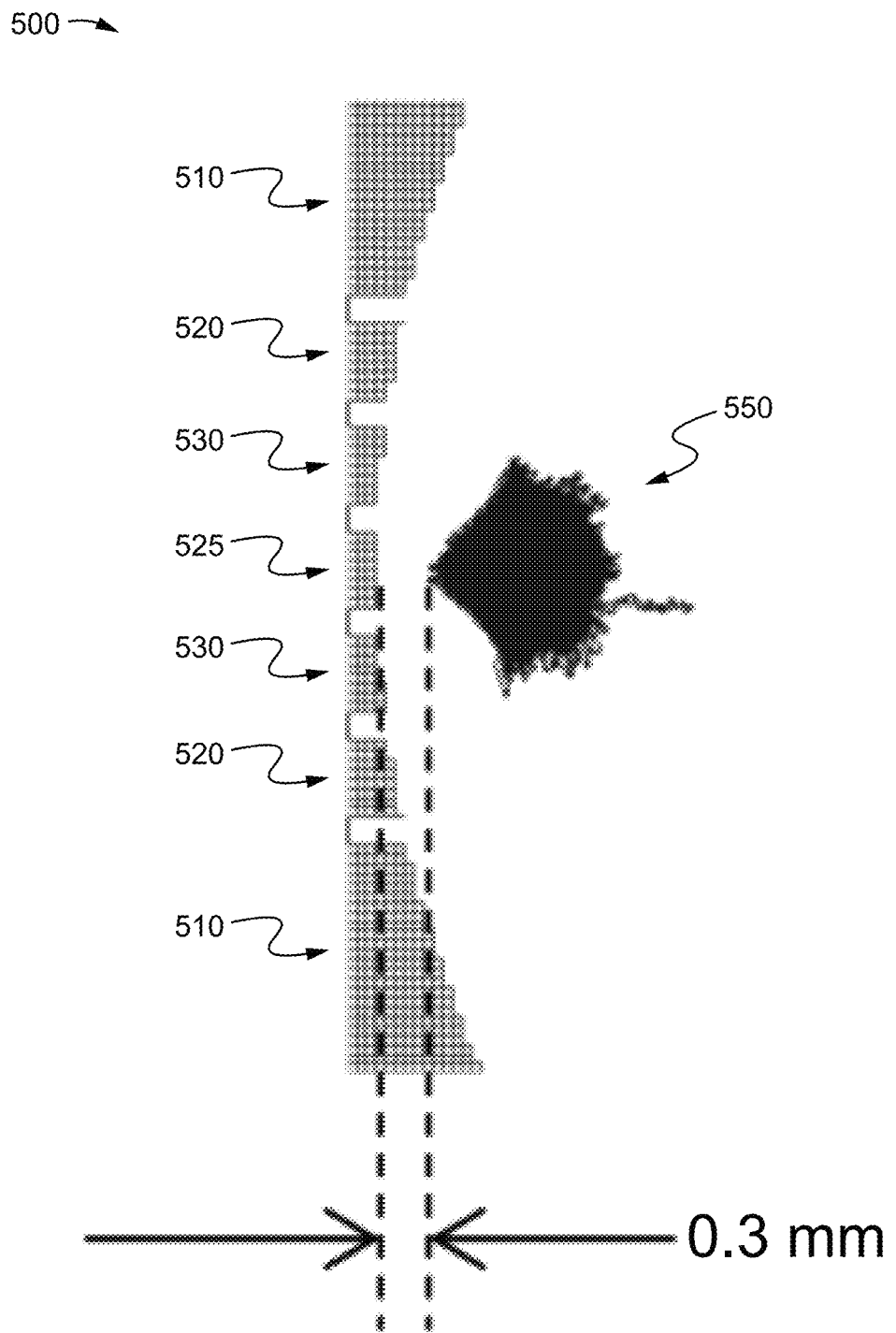
FIG. 5 shows a cross section of the ion mobility device of FIG. 1, with ions moving through the device at a distance from the surface, in accordance with one embodiment of the present invention.

The following description includes the preferred best mode of embodiments of the present invention. It will be clear from this description of the invention that the invention is not limited to these illustrated embodiments but that the invention also includes a variety of modifications and embodiments thereto. Therefore the present description should be seen as illustrative and not limiting. While the invention is susceptible of various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

Disclosed are methods and devices for ion mobility separations. The device has an open structure and may comprise a drift cell formed by a single surface that is not flat or planar. The single surface is thus open and may be curved or angled to form an ion separation channel and help prevent ion losses, which is in contrast to prior drift cells that have two planar surfaces of electrodes forming the channel.

The single, non-planar surface may be formed by curving a flexible printed circuit board material, by three-dimensional printing, or other means to deposit a conductive material on a non-conductive surface.

A combination of RF and DC fields are applied to arrays of electrodes coupled to the surface to create, along with the shape of the curved surface, confining and driving fields that move ions through the device. Lateral confinement is achievable by a combination of electric fields applied to outer electrodes as well as the curvature of the surface.

In one embodiment, two separate arrays of electrodes positioned closer to the middle of the device confine and drive ions throughout the device.

Ions can be driven through the device either by application of static DC field or time-dependent DC field.

The device allows for ion injection at an angle to the plane of ion motion and construction of, in one example, a helical shaped separation device.

The open, non-planar device, which can be curved, also allows for the following: ion introduction at any location in the device; ion current/mobility/mass measurements, as well as optical measurements, at any location in the device; and the non-planar cross section allows non-rectilinear ion path (e.g. helix) which is not possible with planar devices due to the two top and bottom boards.

The device can also include a cover positioned or disposed on the device. On this cover a voltage can be applied to guard against interfering voltage or potential from, e.g., ground or nearby electronics.

Two or more devices can be combined or coupled together, with one device above and offset from the other at an angle, to provide a "waterfall" effect of the ions traveling from one device to another.

FIGS. 1A-1D show different views of an ion mobility device 100 having a single curved or non-planar surface 105 containing arrays of outer DC electrodes 110 and inner DC electrodes 130. The device 100 also includes arrays of RF electrodes 120 and 125 of opposite phase, RF+ and RF−, on either side of the inner DC electrodes 130, in accordance with one embodiment of the present invention. The arrays are coupled to and extend substantially along the length of the surface 105.

In one embodiment, the DC voltage applied to the outer array DC electrodes 110 is the same. The DC voltages applied to the inner array DC electrodes 130 may be different or may be a DC gradient applied across the inner array 130. The DC voltages or fields may be static DC fields or time-dependent DC fields or waveforms.

As shown in FIG. 1, each inner array of DC electrodes 130 is positioned between an adjacent pair—e.g., adjacent RF arrays 120 and 125 or adjacent RF arrays 125 and 120—of the inner array of RF electrodes. Also, a RF waveform on at least one inner array of RF electrodes 120 and 125 is out of phase with a neighboring or adjacent array of RF electrodes 120 or 125. In one embodiment, an inner RF electrode array 120 or 125 is approximately 180 degrees out of phase or phase shifted with its neighboring inner electrode array 120 or 125 to form a pseudopotential.

The surface 105, which is either curved or non-planar, is a single surface. In one embodiment, the surface 105 is not flat and may be comprised of, but is not limited to, a flexible printed board material.

FIGS. 2A-2D show different views of an ion mobility device 200 having a single curved or non-planar surface 205 containing arrays of outer DC electrodes 210 and arrays of inner RF electrodes 220 and 230 with a superimposed DC field on the inner array of RF electrodes 220 and 230, in accordance with one embodiment of the present invention. The RF field on at least one inner electrode array 220 is out of phase with its neighboring inner electrode 230. For example, the RF waveform phase applied to electrode arrays 220 are positive (+), and the RF waveform phase applied to electrode arrays 230 are negative (−). DC gradient or different voltages are applied to the electrodes 210.

FIGS. 3A-3D show different views of an ion mobility device 300 having a single curved or non-planar surface 305 containing arrays of outer DC electrodes 310 and arrays of inner DC electrodes 330 with different DC fields or a DC gradient applied across the arrays of electrodes 310 and 330. The device 300 also includes arrays of RF electrodes 320 and 325 of opposite phase, RF+ or RF−, on either side of the inner DC electrodes 330, in accordance with one embodiment of the present invention. As such, each inner array of DC electrodes 330 is positioned between an adjacent pair of the inner array of RF electrodes 320 and 325.

The DC field applied to the outer array of DC electrodes 310 is different across the outer array 310 or is a DC gradient. The DC field applied to the inner array of DC electrodes 330 is a DC gradient or is different.

FIGS. 4A-4D show different views of an ion mobility device 400 device having a single curved or non-planar surface 405 containing arrays of inner DC electrodes 430 that are offset or misaligned from the arrays of outer DC electrodes 410. Arrays of RF electrodes 420 and 425 of opposite phase (+ or −) are on either side of the inner DC electrodes 430.

The DC field applied to the outer array of DC electrodes 410 and inner array of DC electrodes 430 is different across the outer and inner DC arrays 410 and 430. In one embodiment, a DC gradient is applied across the outer and inner DC arrays 410 and 430. Each inner array of DC electrodes 430 is positioned between an adjacent pair of the inner array of RF electrodes 420 and 425.

FIG. 5 shows a cross section of the ion mobility device 500 of FIG. 1, with ions 550 moving through the device at a distance from the surface, in accordance with one embodiment of the present invention. The device 500 includes an outer array of DC electrodes 510, an inner array of RF electrodes 520 and 525, and an inner array of DC electrodes 530 positioned between array of RF electrodes 520 and 525 of opposite phase (+ or −).

FIG. 5 shows a cross section of the ion mobility device 500 of FIG. 1, with ions 550 moving through the device 500 at a distance from the surface, in accordance with one embodiment of the present invention. The device 500 includes an outer array of DC electrodes 510, an inner array of RF electrodes 520 and 525, and an inner array of DC electrodes 530 positioned between array of RF electrodes 520 and 525 of opposite phase (+ or −).

In the example of FIG. 5, the ions 550 are approximately 0.3 mm from the surface of the device 500. A combination of RF and DC fields applied to the arrays of electrodes 510, 520, 525, and 530, along with the shape of the curved surface, create confining and driving fields that move the ions 550 through the device 500. Lateral confinement is achievable by the curved nature of the surface and application of electric fields to the outer electrodes 510. The inner RF and DC electrode arrays 520, 525, and 530 confine and drive the ions 550 through the device. The ions 550 can be driven either through a static DC field or a time-dependent DC waveform or field.

Figure 6:
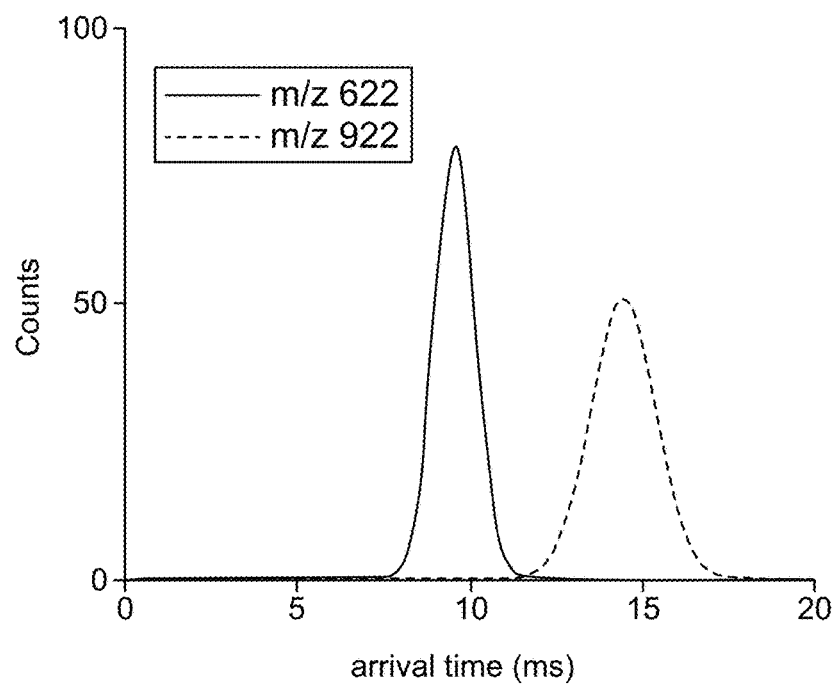
FIG. 6 is a plot of ion counts over arrival time using the embodiment of FIG. 1, showing separation of two ions with different mass-to-charge ratios according to their mobilities.

FIG. 6 is a plot of ion counts over arrival time using the embodiment of FIG. 1, showing the mobility separation of two ions with different mass-to-charge ratios—m/z 622 and m/z 922.

Figure 7A:
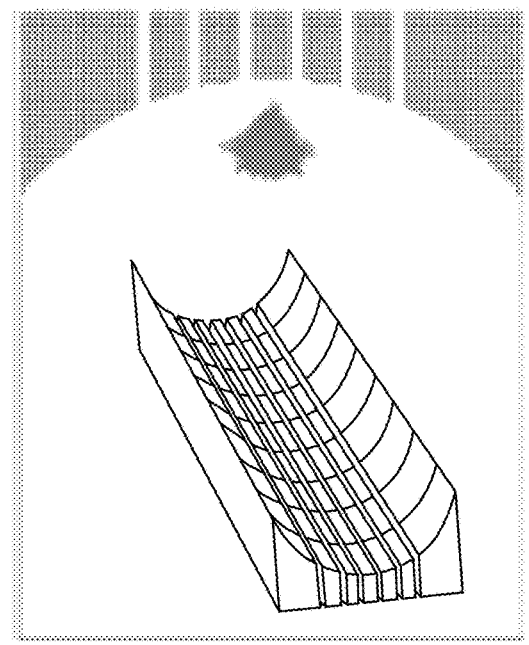
FIG. 7A is a three-dimensional schematic diagram of the device of FIG. 1, with ions moving through the device at a distance from the surface, in accordance with one embodiment of the present invention.

FIG. 7A is a three-dimensional schematic diagram of the device of FIG. 1, with ions moving through the device at a distance from the surface, in accordance with one embodiment of the present invention.

Figure 7C:
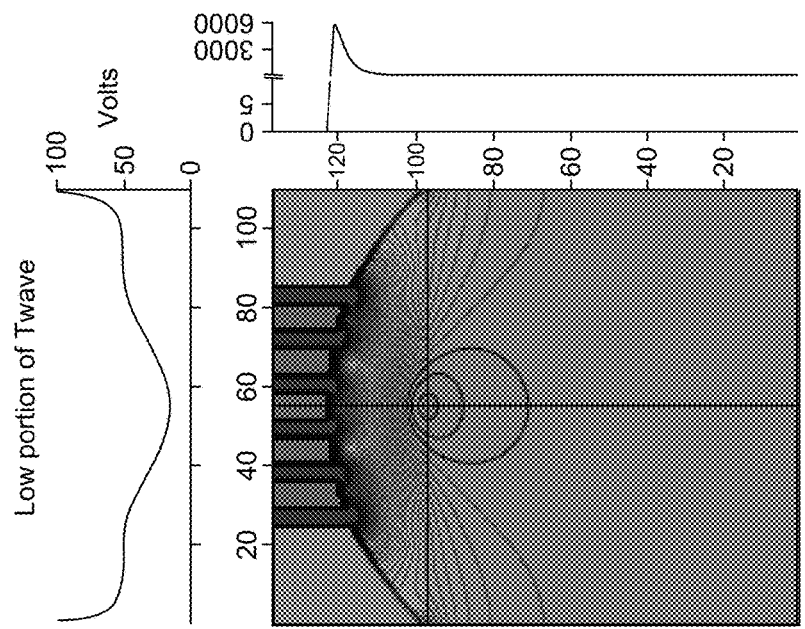
FIG. 7C is a plot showing ion confinement within the device of FIG. 7A at the low portion of a time-dependent electric field.
Figure 7B:
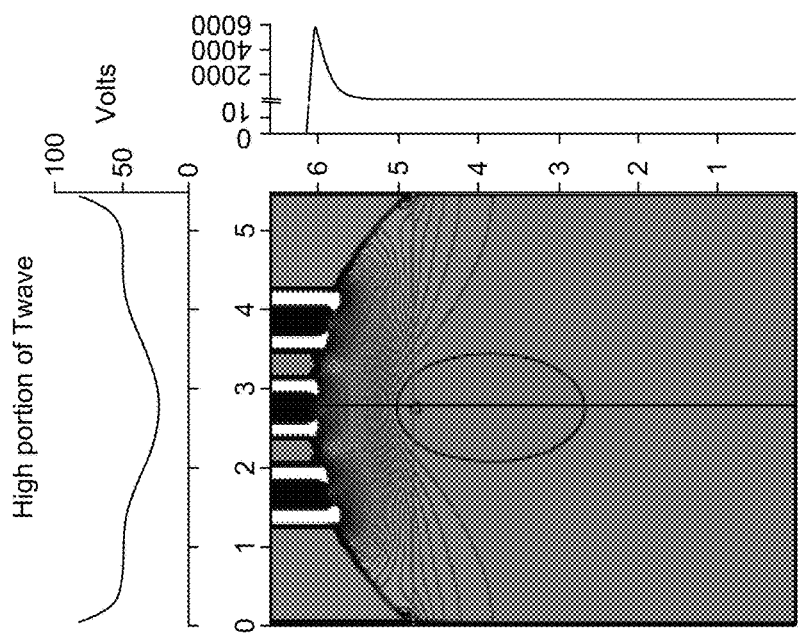
FIG. 7B is a plot showing ion confinement within the device of FIG. 7A at the high portion of a time-dependent electric field.

FIG. 7B is a plot showing ion confinement within the device of FIG. 7A at the high portion of a time-dependent electric field, a dynamic electric field.

FIG. 7C is a plot showing ion confinement within the device of FIG. 7A at the low portion of a time-dependent electric field, a dynamic electric field.

Figure 8:
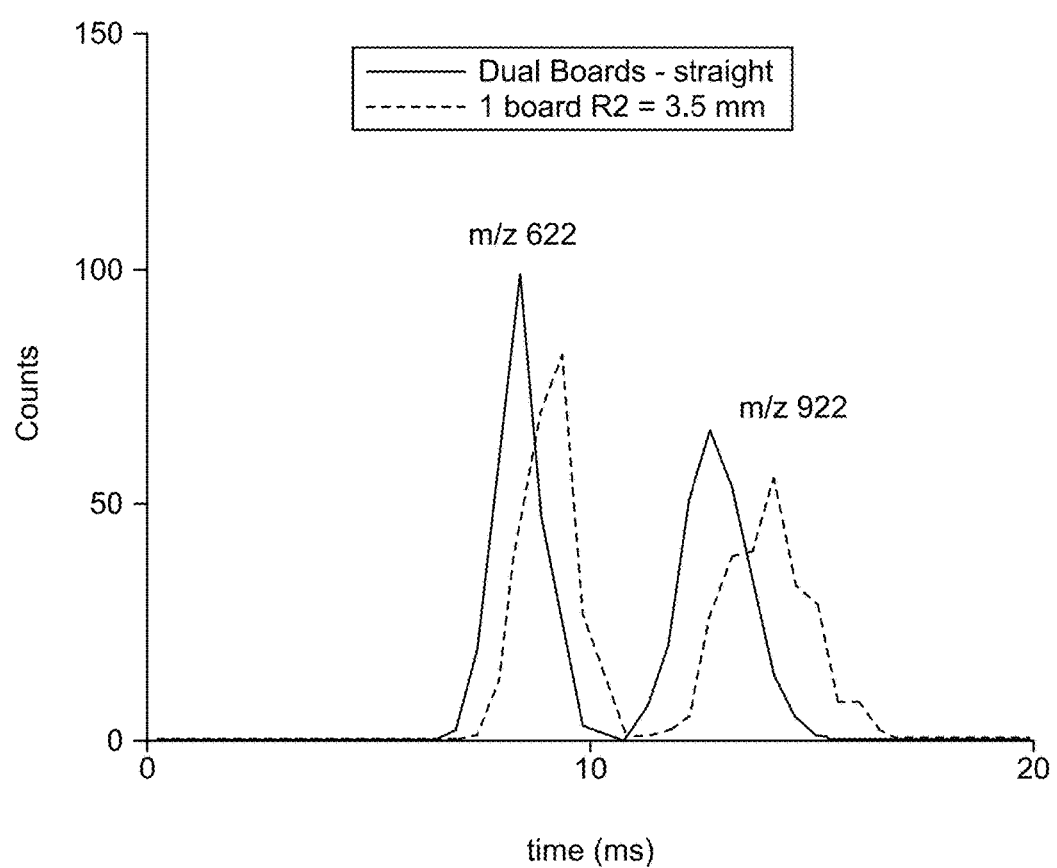
FIG. 8 is a plot of ion counts over arrival time of two ions with different mass-to-charge ratios, and separated according to their mobilities, using two different configurations—the embodiment of FIG. 4 or a single board ion mobility separation device and a prior dual board ion mobility separation device.

FIG. 8 is a plot of ion counts over arrival time of two ions with different mass-to-charge ratios (m/z 622 and m/z 922) using two different configurations—the embodiment of FIG. 4 or a single board ion mobility separation device and a prior dual board ion mobility separation device. The prior dual boards are straight or planar, while the single board configuration is curved. The length of each device is approximately 76 mm.

Figure 9A:
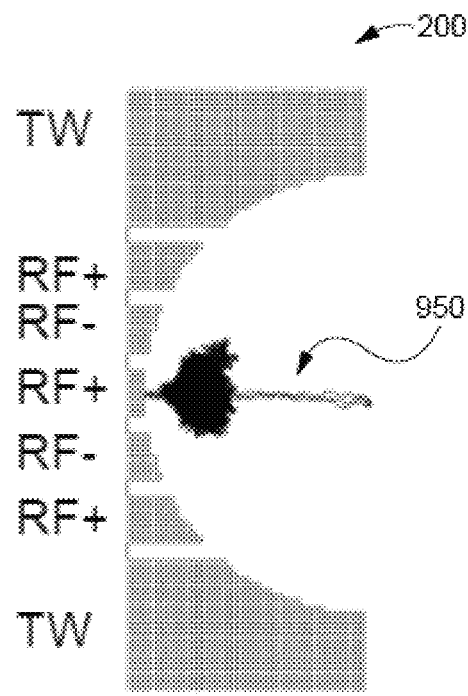
FIGS. 9A-9B show cross section and perspective views of the ion mobility device of FIG. 2, with ions moving through the device at a distance from the surface, with a DC traveling wave field applied to the outside electrodes and opposing phases of RF applied to the inner electrodes, in accordance with one embodiment of the present invention.
Figure 9B:
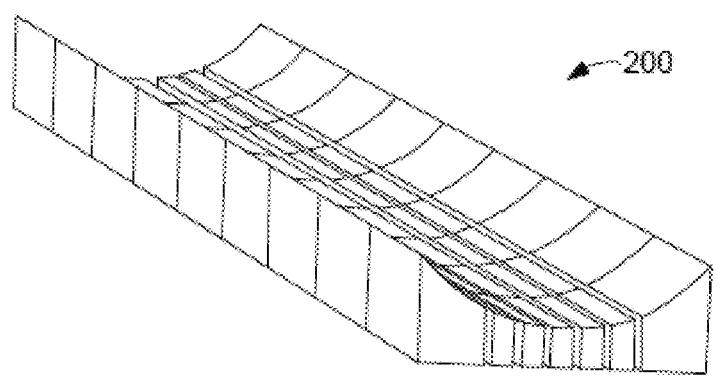

FIGS. 9A-9B show cross section and perspective views of the ion mobility device 200 of FIGS. 2A-2D, with ions 950 moving through the device 200 at a distance from the surface 205, with a DC traveling wave field (TW) applied to the outer DC electrodes 210 and opposing phases of RF (RF+/RF−) applied to the inner RF electrodes 220, 230, in accordance with one embodiment of the present invention.

Figure 10A:
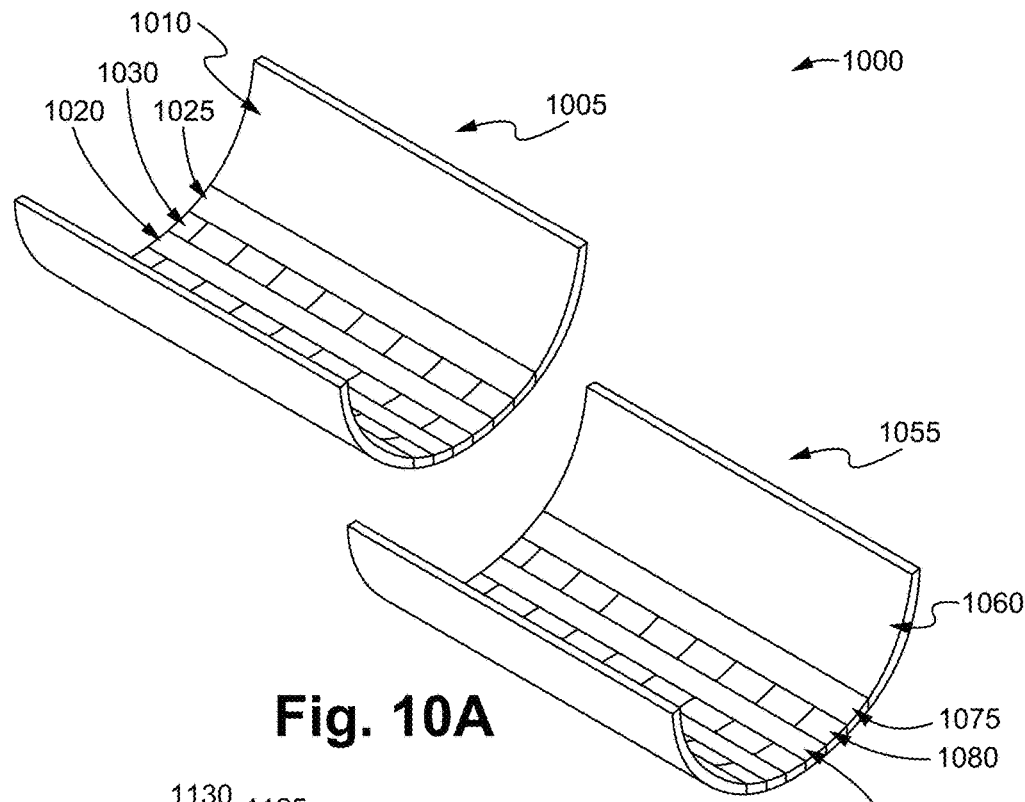
FIG. 10A is a perspective view schematic diagram of two devices, each similar to the embodiment shown in FIGS. 1A-D, with one device above and offset from the other at an angle, to provide a "waterfall" effect of the ions traveling from one device to the other.

FIG. 10A is a perspective view schematic diagram of two devices 1005 and 1055 used in combination as an ion mobility separation device or apparatus 1000. Each device 1005 and 1055 is similar to the embodiment shown in FIGS. 1A-D, with one device 1005 above and offset from the other 1055 at an angle, to provide a "waterfall" effect of the ions traveling from one device to the other.

The device 1005 includes outer arrays of DC electrodes 1010, inner arrays of DC electrodes 1030, and arrays of RF electrodes 1020 and 1025. Each inner array of DC electrodes 1030 is positioned between an array of RF electrodes 1020 and 1025 having opposite phases (RF+ or RF−).

The device 1055 includes outer arrays of DC electrodes 1060, inner arrays of DC electrodes 1080, and arrays of RF electrodes 1070 and 1075. Each inner array of DC electrodes 1080 is positioned between an array of RF electrodes 1070 and 1075 having opposite phases (RF+ or RF−).

Figure 10B:
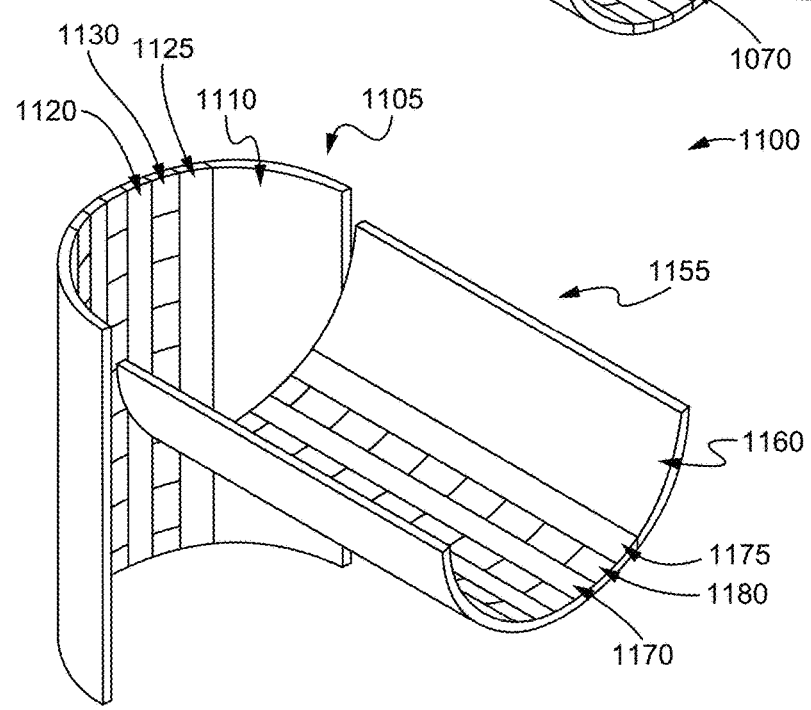
FIG. 10B is a perspective view schematic diagram of two devices, each similar to the embodiment shown in FIGS. 1A-D, with the devices positioned orthogonally to one another, to provide a "waterfall" effect of the ions traveling from one device to the other.

FIG. 10B is a perspective view schematic diagram of two devices 1105 and 1155 used in combination as an ion mobility separation device or apparatus 1100. Each device 1105 and 1155 is similar to the embodiment shown in FIGS. 1A-D, with the devices 1105 and 1155 positioned orthogonally to one another, to provide a "waterfall" effect of the ions traveling from one device to the other.

The device 1105 includes outer arrays of DC electrodes 1110, inner arrays of DC electrodes 1130, and arrays of RF electrodes 1120 and 1125. Each inner array of DC electrodes 1130 is positioned between an array of RF electrodes 1120 and 1125 having opposite phases (RF+ or RF−).

The device 1155 includes outer arrays of DC electrodes 1160, inner arrays of DC electrodes 1180, and arrays of RF electrodes 1170 and 1175. Each inner array of DC electrodes 1180 is positioned between an array of RF electrodes 1170 and 1175 having opposite phases (RF+ or RF−).

While a number of embodiments of the present invention have been shown and described, it will be apparent to those skilled in the art that many changes and modifications may be made without departing from the invention in its broader aspects. The appended claims, therefore, are intended to cover all such changes and modifications as they fall within the true spirit and scope of the invention.

We claim:

1. An ion mobility separation or manipulation device comprising:
   a. a single, non-planar surface that is curved to form an ion separation channel;
   b. arrays of electrodes coupled to the surface; and
   c. a combination of RF and DC voltages applied to the arrays of electrodes to create confining and driving fields that move ions through the device;
      wherein the electrodes receiving the applied RF and DC voltages conform to the shape of the surface.

2. The device of claim 1 further comprising one or more surfaces and/or electrodes external to the device to create additional electric fields on the device.

3. The device of claim 2 wherein voltages applied to the external surfaces and/or electrodes are turned on or turned off.

4. The device of claim 1 wherein the arrays of electrodes coupled to the surface extend above the surface and vary in the distance above the surface.

5. The device of claim 2 wherein one or more of the arrays of electrodes coupled to the surface are turned on or turned off by the external surfaces and/or electrodes.

6. The device of claim 1 wherein the single, non-planar surface includes arrays of electrodes on each side of the single, non-planar surface.

7. The device of claim 1 wherein the device is located in a partially or completely transparent cover or enclosure.

8. The device of claim 1 wherein the single, non-planar surface is one of the following shapes: cylindrical, a spiral, a funnel, hemispherical, or elliptical.

9. The device of claim 1 wherein the arrays of electrodes comprise one or more arrays of inner RF electrodes and a plurality of arrays of outer DC electrodes, wherein the inner array of RF electrodes and the outer array of DC electrodes extend substantially along the length of the surface.

10. The device of claim 9 wherein a first outer array of DC electrodes is positioned on one side of the inner array of RF electrodes, and a second outer array of DC electrodes is positioned on the other side of the inner array of RF electrodes.

11. The device of claim 9 wherein the DC voltages are applied to the first and second outer electrode arrays, and wherein the RF voltages are applied to the inner array of electrodes.

12. The device of claim 11 wherein the RF voltage on at least one inner electrode array is out of phase with its neighboring inner electrode.

13. The device of claim 12 wherein the RF voltage applied to each inner electrode array is phase shifted with its neighboring inner electrode to form a pseudopotential.

14. The device of claim 13 wherein the RF voltage applied to the inner electrode array is approximately 180 degrees out of phase with its neighboring inner electrode array to form the pseudopotential.

15. The device of claim 10 further comprising one or more arrays of inner DC electrodes extending substantially along the length of the surface, wherein each inner array of DC electrodes is positioned between an adjacent pair of the inner array of RF electrodes.

16. The device of claim 15 wherein a RF voltage on at least one inner array of RF electrodes is out of phase with a neighboring or adjacent inner array of RF electrodes.

17. The device of claim 16 wherein a first DC voltage applied to the outer array of DC electrodes is the same, and a second DC voltage applied to the inner array of DC electrodes is a DC gradient or different across the inner DC arrays.

18. The device of claim 16 wherein a first DC voltage applied to the outer array of DC electrodes is different across the outer array or is a DC gradient, and a second DC voltage applied to the inner array of DC electrodes is a DC gradient or different across the inner DC arrays.

19. The device of claim 18 wherein the inner array of DC electrodes is misaligned or offset from the outer array of electrodes.

20. The device of claim 10 further comprising a superimposed DC field on the inner arrays of RF electrodes.

21. The device of claim 20 wherein the RF voltage on at least one inner RF electrode array is out of phase with its neighboring inner RF electrode array.

22. The device of claim 1 wherein the DC voltages are static DC voltages or time-dependent DC waveforms.

23. A method of separating or manipulating ions in gas phase comprising:
   a. coupling arrays of electrodes to a single, non-planar surface that is curved to form an ion separation channel; and
   b. applying a combination of RF and DC voltages to the arrays of electrodes to create confining and driving fields that move ions through the single, non-planar surface;
      wherein the electrodes receiving the applied RF and DC voltages conform to the shape of the surface.

24. The method of claim 23 further comprising creating additional electric fields on the device via one or more surfaces and/or electrodes external to the device.

25. The method of claim 24 wherein voltages applied to the external surfaces and/or electrodes are turned on or off.

26. The method of claim 23 wherein the arrays of electrodes coupled to the surface extend above the surface and vary in the distance above the surface.

27. The method of claim 24 further comprising turning on or turning off at least one of the arrays of electrodes coupled to the surface by the external surfaces and/or electrodes.

28. The method of claim 23 wherein the single, non-planar surface includes arrays of electrodes on each side of the single, non-planar surface.

29. The method of claim 23 further comprising disposing the device in a partially or completely transparent cover or enclosure.

30. The method of claim 23 wherein the single, non-planar surface is one of the following shapes: cylindrical, a spiral, a funnel, hemispherical, or elliptical.

31. The method of claim 23 wherein the arrays of electrodes comprises one or more arrays of inner RF electrodes and a plurality of arrays of outer electrodes, wherein the inner array of RF electrodes and the outer array of DC electrodes extend substantially along the length of the surface.

32. The method of claim 31 wherein a first outer array of DC electrodes is positioned on one side of the inner array of RF electrodes, and a second outer array of electrodes is positioned on the other side of the inner array of electrodes.

33. The method of claim 31 wherein the DC voltages are applied to the first and second outer electrode arrays, and wherein the RF voltages are applied to the inner array of electrodes.

34. The method of claim 33 wherein the RF voltage on at least one inner electrode array is out of phase with its neighboring inner electrode array.

35. The method of claim 34 wherein the RF voltage applied to each inner electrode array is phase shifted with its neighboring inner electrode array to form a pseudopotential.

36. The method of claim 35 wherein the RF voltage applied to the inner electrode array is approximately 180 degrees out of phase with its neighboring inner electrode array to form the pseudopotential.

37. The method of claim 32 further comprising providing one or more arrays of inner DC electrodes extending substantially along the length of the surface, wherein each inner array of DC electrodes is positioned between an adjacent pair of the inner array of RF electrodes.

38. The method of claim 37 wherein a RF voltage of at least one inner array of RF electrodes is out of phase with a neighboring or adjacent inner array of RF electrodes.

39. The method of claim 38 wherein a first DC voltage applied to the outer array of DC electrodes is the same, and a second DC voltage applied to the inner array of DC electrodes is a DC gradient or different across the inner DC array.

40. The method of claim 38 wherein a first DC voltage applied to the outer array of DC electrodes is different across the outer array or is a DC gradient, and a second DC voltage applied to the inner array of DC electrodes is a DC gradient or different across the inner DC arrays.

41. The method of claim 40 wherein the inner array of DC electrodes is misaligned or offset from the outer array of electrodes.

42. The method of claim 32 further comprising superimposing a DC electric field on the inner arrays of RF electrodes.

43. The method of claim 23 wherein the ions are introduced from the outside at an angle to the surface.

44. The method of claim 23 wherein the DC voltages are static DC voltages or time-dependent DC waveforms.

45. An ion mobility separation or manipulation device comprising:
 a. a single non-planar surface that is curved to form an ion separation channel;
 b. arrays of electrodes including one or more arrays of inner RF electrodes and a plurality of arrays of outer DC electrodes, coupled to the single surface, wherein the inner array of RF electrodes and the outer array of DC electrodes extend substantially along the length of the single surface, wherein a first and second outer array of DC electrodes is positioned on either side of the inner array of RF electrodes;
 c. one or more arrays of inner DC electrodes extending substantially along the length of the surface, wherein each inner array of DC electrodes is positioned between an adjacent pair of the inner array of RF electrodes; and
 d. a combination of RF and DC voltages applied to the arrays of electrodes to create confining and driving fields that move ions through the device;
  wherein the one or more arrays of inner RF electrodes, the plurality of arrays of outer DC electrodes, and one or more arrays of inner DC electrodes conform to the shape of the surface.

46. The device of claim 45 wherein a RF voltage on at least one inner array of RF electrodes is out of phase with a neighboring or adjacent inner array of RF electrodes.

47. The device of claim 45 wherein a first DC voltage applied to the outer array of DC electrodes is the same, and a second DC voltage applied to the inner array of DC electrodes is a DC gradient or different across the inner DC array.

48. The device of claim 45 wherein a first DC voltage applied to the outer array of DC electrodes is different across the outer array or is a DC gradient, and a second DC voltage applied to the inner array of DC electrodes is a DC gradient or different across the inner DC arrays.

49. The device of claim 46 wherein the inner array of DC electrodes is misaligned or offset from the outer array of electrodes.

50. An ion mobility separation or manipulation device comprising:
 a. a single non-planar surface that is curved to form an ion separation channel;
 b. arrays of electrodes including one or more arrays of inner RF electrodes and a plurality of arrays of outer DC electrodes, coupled to the single surface, wherein the inner array of RF electrodes and the outer array of DC electrodes extend substantially along the length of the single surface, wherein a first and second outer array of DC electrodes is positioned on either side of the inner array of RF electrodes;
 c. a combination of RF and DC voltages applied to the arrays of electrodes to create confining and driving fields that move ions through the device; and
 d. a superimposed DC field on the inner arrays of RF electrodes to further confine and move the ions through the device;
  wherein the one or more arrays of inner RF electrodes, the plurality of arrays of outer DC electrodes, and one or more arrays of inner DC electrodes conform to the shape of the surface.

51. An ion mobility separation or manipulation apparatus comprising:
 a. at least two non-planar surfaces that are curved to form an ion separation channel extending therebetween;
 b. arrays of electrodes coupled to the at least two surface; and
 c. a combination of RF and DC voltages applied to the arrays of each surface to create confining and driving fields that move ions from one surface to another, thus providing a "waterfall" effect of the ions moving through each surface;
  wherein the electrodes receiving the applied RF and DC voltages conform to the shape of the surfaces to which they are coupled.

52. The apparatus of claim 51, wherein one of the surfaces is positioned above and offset from the other at an angle.

53. The apparatus of claim 51, wherein the at least two surfaces are orthogonal to one another.

* * * * *